United States Patent [19]

Self et al.

[11] Patent Number: 5,661,029
[45] Date of Patent: Aug. 26, 1997

[54] BIOLOGICAL CULTURE GROWTH AND OBSERVATION DEVICE

[75] Inventors: Jim Self, San Jose; Robert D. Hall; R. Daniel Webster, both of Sunnyvale, all of Calif.

[73] Assignee: Biomed, San Jose, Calif.

[21] Appl. No.: 242,014

[22] Filed: May 12, 1994

[51] Int. Cl.$^6$ .................................................. C12M 3/00
[52] U.S. Cl. ................... 435/288.3; 435/288.4; 435/288.7; 435/305.4; 359/398
[58] Field of Search ....................... 435/284, 291, 435/298, 287.1, 288.3, 288.4, 288.7, 305.4; 422/102; 359/398

[56] References Cited

U.S. PATENT DOCUMENTS

| | | | |
|---|---|---|---|
| 3,726,767 | 4/1973 | White | 195/127 |
| 4,271,270 | 6/1981 | Lukaesek | 435/294 |
| 4,396,717 | 8/1983 | Fiebig et al. | 435/301 |
| 4,867,316 | 9/1989 | Rollender et al. | 206/670 |
| 5,173,298 | 12/1992 | Meadows | 424/427 |
| 5,417,576 | 5/1995 | Hill | 435/299 |

FOREIGN PATENT DOCUMENTS

IT92/00121  10/1992  WIPO.

*Primary Examiner*—David A. Redding
*Attorney, Agent, or Firm*—Wilson Sonsini Goodrich & Rosati

[57] ABSTRACT

A biological culture growth and observation system provides for the growth of a biological sample in a growth medium, and the observation of the grown sample (organism) through a microscope objective once growth is sufficient as to permit discrimination of the biological sample. Observation and growth is achieved in a single device. The system includes a tray with a top, and a sealable section on the top. Included within the tray is a depression, or well, that receives the growth medium to grow the biological organism in the well. A lid is sealable and resealable around the sealable section on the top of the tray. An interior side of the lid, that faces the growth medium, does not fog up in the presence of the growth medium. Optionally included is a barrier layer that is positioned over the well. The barrier layer minimizes evaporation from the growth medium and permits the biological culture growth and observation system to have a long shelf life.

62 Claims, 4 Drawing Sheets

BIOLOGICAL CULTURE GROWTH AND OBSERVATION DEVICE

BACKGROUND OF THE INVENTION

1. Field of the Invention

This invention relates generally to the growth and observation of biological cultures, and more particularly to a device that provides for the observation and growth of the biological culture in a one device.

2. Description of Related Art

Growth media are used for a variety of different organisms, including but not limited to fungi, bacteria, protozoa, and the like, in order to grow a microbiological sample in the medium. The biological culture is permitted to grow in or on the growth medium, and it is then observed for identifying characteristics.

Currently, this is generally performed in a test tube with the growth medium in the tube on a slant. A variety of media is used. One example of a class of growth media is the dermatophytes test medium which include color change agents. As soon as the biological sample affects the medium the medium begins to change color. The microbiologist then removes the biological sample from the tube and spreads it on a growth medium located on a glass slide. A glass cover slip is positioned over the biological sample, permitting the biological sample to grow. After identifiable growth occurs, the biological sample is treated with phenyl cotton blue so it does not become contagious. This kills the biological sample, but it is still observable. The growth sample is then removed from the medium and observed with a microscope.

One of the difficulties with this method is that as the biological sample grows, an identifying structure, a very delicate flowering portion of the dermatophyte or fungi, grows and it is easy to destroy. Merely breathing on it can destroy it.

Removal of such a biological sample with its delicate identifying structure from a device adaped for growth, to a device that is suitable for observation, presents numerous problems. There are too many opportunities to damage the sample, making it difficult, or impossible to observe and therefore characterize. This method, and devices associated with this method, are unreliable, unpredictable, time consuming and expensive.

There is a need for an improved device that permits the growth, transportion and observation of the delicate biological structures while minimizing damage to the biological structure. Further, it would be desirable to provide a biological culture growth, transportation and observation system that performs the functions of culture growth, transportation and identification in one device.

SUMMARY OF THE INVENTION

It is an object of the present invention to provide a biological culture growth and observation system that provides for the growth of a biological culture, as well as its identification in one device.

Another object of the present invention is to provide a biological culture growth and observation system that is its own, (i) transport device, (ii) observation platform, (iii) growth platform, and (iv) integral unit for the biological culture growth and disposal.

These and other objects of the present invention are achieved in a biological culture growth and observation system that includes a tray with a resealable top. The tray further includes a depression or well to contain a growth medium in which to grow an organism. An optically clear lid is sealable, and resealable, around the top of the tray. An interior side of the lid that faces the growth medium, does not fog up.

The biological culture growth and observation system can also include a separate barrier layer sealed over the medium well. The barrier layer minimizes evaporation from the growth medium and permits the growth and observation system to have an extended shelf life. When the growth medium is deposited in the well, vapors from the growth medium can begin to evaporate. If this remains unchecked, then the growth medium dries out, and is of little use to serve as the medium in which to grow the biological sample.

The growth medium is placed in the well of the system. It is then covered with the barrier layer in a manner that vapor is not permitted to escape from the well. The lid is then sealed to the tray. The biological culture growth and observation system now has an extended shelf life. When it is desired to use the device, the lid is peeled back, the barrier layer removed, and a biological sample introduced onto the growth medium. The lid is then resealed in the original position. The biological sample grows in the growth medium and the interior side of the lid does not fog up as the biological sample grows. The biological sample may grow up to or on the interior side of the lid, but this is not always the case.

Once the growth is complete enough for observation and identification, the biological culture growth and observation system is placed on a microscope stage and viewed through the lid without opening it. The biological sample is then identified and if there is no further need to keep the biological sample, the entire growth and observation system is disposed of.

The well is shallow enough to permit light to pass through the well and medium for observation with a microscope that views through the clear lid. There are numerous ways of sealing the lid to the top of the tray. Resealable adhesives can be employed, a mechanical seal is possible, the lid and tray can be sealed by a thermal bond, or the lid and tray can be welded by use of a layer of solvent.

Optionally, gas passages can be included in the biological culture growth and observation system. When the barrier layer is removed, the gas passages introduce a suitable gas, including but not limited to air, $CO_2$ and the like, into the well containing the growth medium and the biological sample.

Accordingly, the present invention is a biological culture growth and observation system that provides for culture and identification of a biological sample in one device. It serves as its own transport device, growth platform, observation platform, in a single disposable unit.

Other aspects and advantages of the present invention can be seen upon review of the figures, the detailed description, and the claims which follow.

DETAILED DESCRIPTION OF THE PREFERRED EMBODIMENTS

Figure 1:
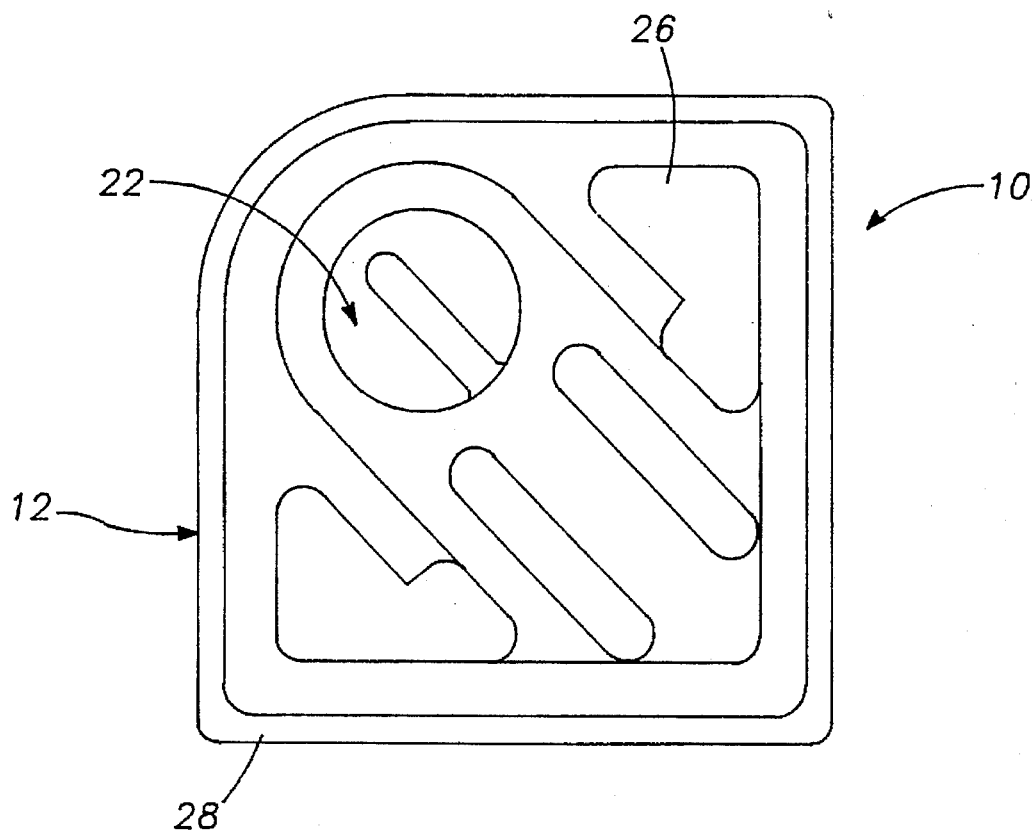
FIG. 1 is a plan view of the biological culture growth and observation system according to the present invention.
Figure 2:
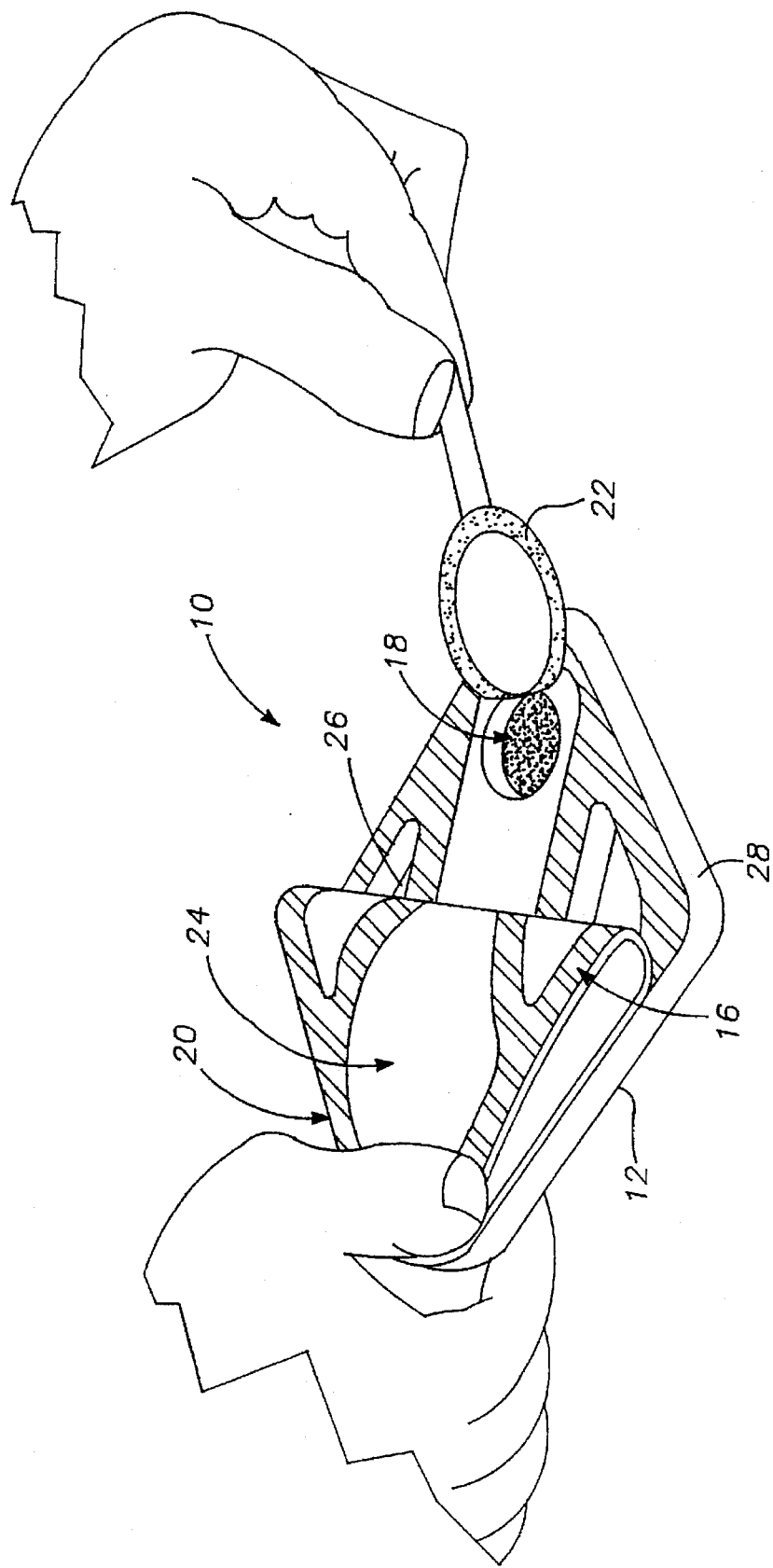
FIG. 2 is a perspective view of the biological culture growth and observation system with the lid pulled back according to the present invention.
Figure 3:
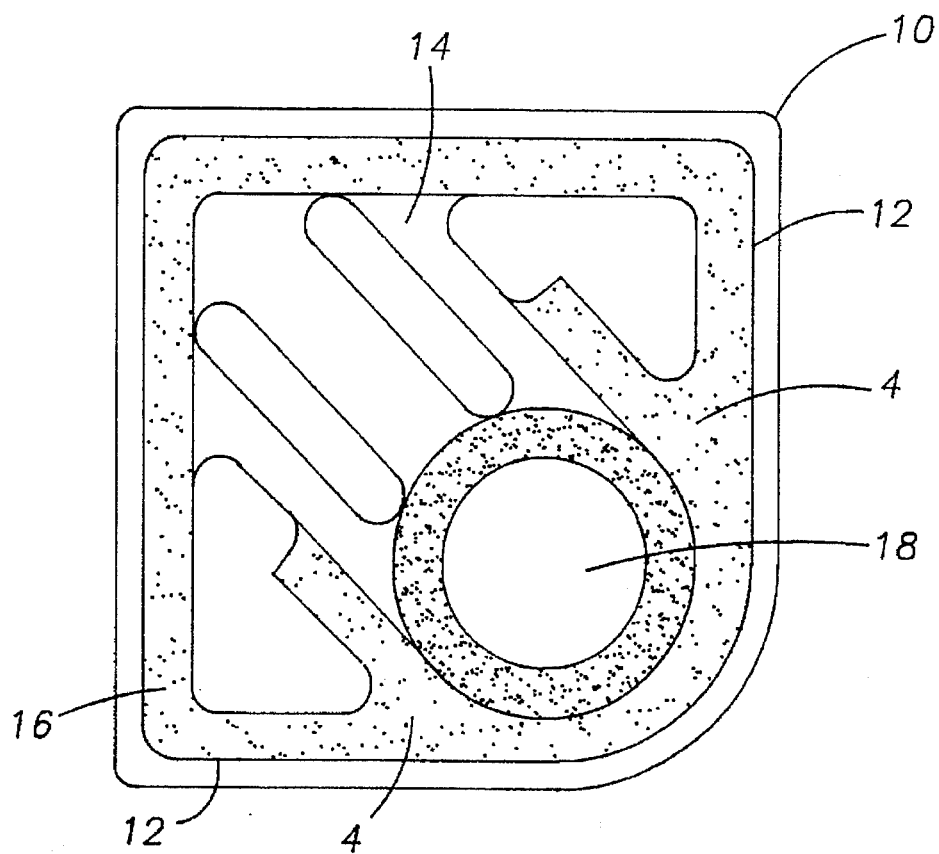
FIG. 3 is a top down view of the biological culture growth and observation system according to the present invention.

Referring now to FIGS. 1 and 2, a biological culture growth and observation system 10 includes a tray 12 with a top 14 that includes a sealable section 16. A depression or well 18 (FIG. 3) is included in tray 12 to receive a growth medium, not shown, to grow any variety of organisms in well 18. Well 18 can be formed as an integral part of tray 12 or it can be a separate section that is attached to tray 12. Well 18 includes both side and bottom walls. It will be appreciated that well 18 may take a variety of forms, including but not limited to, (i) a single flat bottom depression, (ii) a depression with an adjoining raised area, (iii) a flat surface covered with a thin film of growth medium, (iv) a multi-cavity depression wherein each cavity holds a distinct medium and (v) a multi-cavity depression in which each cavity holds a distinct growth medium and there is another medium over the entire multi-cavity depression.

Any number of different biological organisms can be grown in well 18 including but not limited to fungi bacteria, yeast and the like. It will be appreciated that the invention is not limited to these specific biological organisms.

A lid 20, that is both sealable and resealable around sealable section 16, is included. Lid 20 has an interior side 24, shown in FIG. 2, that faces the growth medium in well 18 but does not fog up upon vapor condensation. When a biological sample is placed in a culture medium in well 18, vapors can be created. Interior side 24 is either a coated material such as Vistex-75, available from Film Specialties, Inc. Whitehorn, N.J., or lid 20 is formed of a material that does not permit fogging. Both sides of lid do not have to meet this requirement, only interior side 24 must possess the non-fogging properties.

Figure 4:
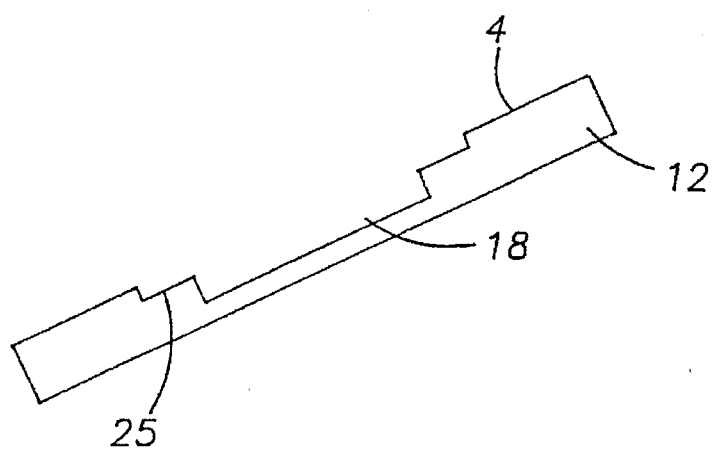
FIG. 4 is a sectional view of the biological culture growth and observation system, taken along the lines 4—4 in FIG. 3 according to the present invention.

A barrier layer 22 is positioned over well 18 to minimize evaporation from the growth medium. Barrier layer 22 is initially positioned over well 18 on a shoulder 25 (FIG. 4) in a manner so that the culture medium does not dry out while biological culture growth and observation system 10 is stored. A suitable barrier layer is available from LamaShield, Product No. 8034, Cleveland, Ohio. Barrier layer 22 can also include a tab which the operator pulls in order to remove barrier layer 22 from the top of well 18. Barrier layer 22 is removed just before the biological sample is added to the culture medium. Lid 20 is first pulled back in a direction away from tray top 14 in an amount sufficient so that barrier layer 22 can be removed, and the biological sample added to the culture medium. Barrier layer 22 is then discarded, and lid 20 is then again sealed to tray top 14 at sealable section 16. It should be noted that sealable section 16 can be at the peripheral edge of tray top 14, or it may on any area of tray top 14. In certain applications air passages 26 are included and formed between tray top 14 and lid 20 when the two are sealed together. Air passages introduce a gas, including but not limited to air or $CO_2$, that promotes the growth of the bacterial sample in the culture medium.

Biological culture growth and observation system 10 is designed so that the biological sample can grow up and spread across the surface of the culture medium, and in certain instances spread across portions of tray top 14, possibly reach interior side 24 of lid 20, and may even grow right on interior side 24. The grown biological sample is identified by its structure and is viewed through a microscope objective. In many instances, microscopic structures will be the point of discrimination, There is a point where it is possible to discriminate the biological sample after it has grown. This is done visually through the use of a microscope. With dermatophytes, there may be a color change in the culture medium. It will be appreciated that the present invention is applicable to a variety of different microscopes and powers. Lid 20 must be thinner than the working distance between the objective lens and the object to be viewed Significantly, biological culture growth and observation system 10 performs two functions in one device. It cultures and identifies a biological sample. It also serves as its own transport device, observation platform, growth platform, and as a single disposal unit for the biological sample, culture medium and the substrate on which all of this takes place.

The amount of biological sample placed in well 18 can be in the milligram range. Only a small amount of biological sample may be necessary such as but not limited to, two or three hair follicles, a piece of a toe nail, or a simple skin scrapping. It can be a single organism, or thousands of organisms.

Biological culture growth and observation system 10 reduces an operator's exposure to the biological sample. There are certain biological samples that can be hazardous to humans. Biological culture growth and observation system 10 does not require the transfer of the culture medium with the biological sample to a slide, and thus is a device that performs two functions and reduces operator exposure.

The present invention is suitable for substantially any culture medium that supports the growth of the biological organism. Such culture media are well known to those skilled in the art.

Tray 12 is made of a material that provides sufficient support for the culture medium and the growth of the biological organism in well 18, It is preferably thermally formable, optically transparent in order to transmit light, non reactive with the culture medium and does not permit the transport of oxygen or water vapor. Suitable materials include glasses, plastics including but not limited to Polystryene, PETG, Polypropolene, and the like. Accordingly, the bottom of well 18 is also optically transparent.

In one embodiment, tray 12 has an outer trim dimension of about 3.25 inches, a height of about 0.25 inches that is created by an underside lip 28, the bottom of well 18 to the top of tray 12 is 0.14 inches, the depth of well 18 is about 0.12 inches and the diameter of well 18 is 1 inch. It will be appreciated that there are any number of variations to these dimensions, and the present invention is not to be limited by any or all of the dimensions. Well 18 must be thin enough so that light can penetrate through it and the growth medium in order for an operator to view the grown biological organism through a microscope objective. Lid 20 may dimensionally extend beyond tray top 14 to facilitate the ability to pull lid 20 away from tray top 14.

Lid 20 is made of a material combination/lamination that is capable of being resealed to sealable section 16, has optical transparency, is non-toxic to biological organisms, and has interior side 24 that does not fog up. Suitable materials include optically transparent plastics including but not limited to polyurethane, PET, PP, Polypropolyene and the like.

The seal formed between lid 20 and sealable section 16 must be sufficient that organisms do not migrate out of biological culture growth and observation system 10. The seal may be a microbial barrier, but it is not necessary that it be of this nature.

Lid 20 and tray top 14 can be sealed in a number of ways. An adhesive can be employed such as acrylic based adhesives. Suitable adhesives include but are not limited to 3M 9374, available from 3M. Lid 20 can also be mechanically sealed, sealed by a thermal bond, or even welded with the use of a layer of solvent. The solvent can be placed on lid 20 or tray top 14, and then become dissolved in order to create the weld.

Figure 5:
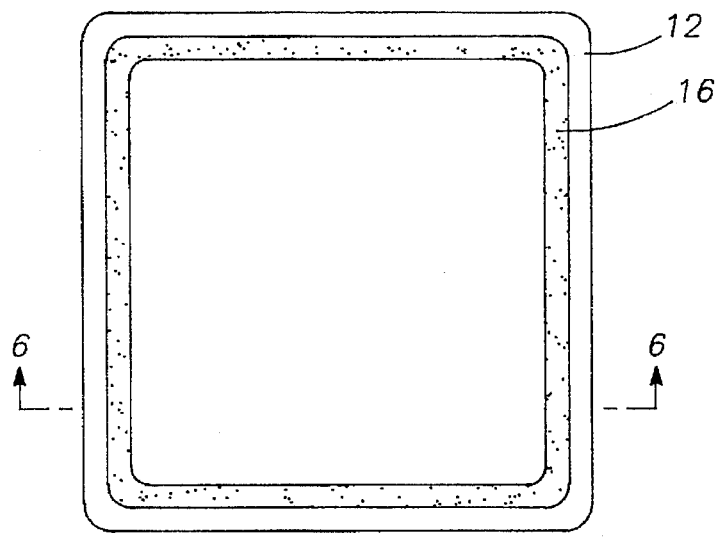
FIG. 5 is a top down view of the resealable lid with a mechanical closure according to the present invention.
Figure 6:
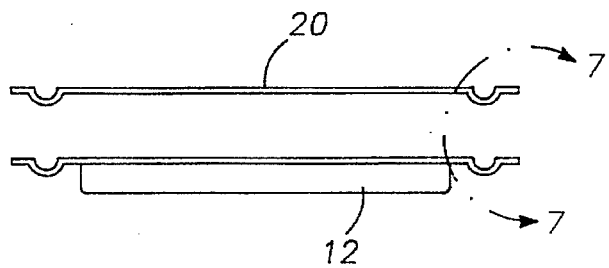
FIG. 6 is a sectional view of the resealable lid with the mechanical closure taken along the lines 6—6 of FIG. 5 according to the present invention.
Figure 7:
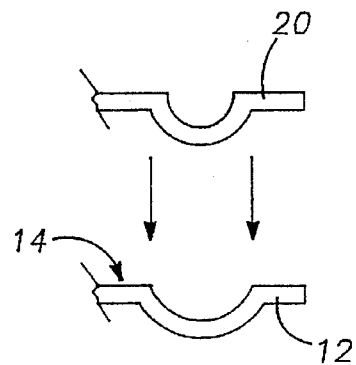
FIG. 7 is a detailed sectional view of the lid and the tray, with a frictional fit mechanical closure, according to the present invention.

FIGS. 5 through 7 illustrate a mechanical interlock seal between lid 20 and tray 12. The two are engaged in a friction fit to form a mechanical closure.

In one embodiment lid 20 can include or incorporate an optical lens.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

We claim:

1. A device for growing and observing a microbiological culture, comprising:
   a substrate with a top and a substrate periphery around the top, the substrate further including a well to provide a containment and barrier for a growth medium to grow an organism in the substrate, and the well including a well periphery;
   a lid that is sealable and resealable around the substrate periphery, the lid including an interior side that sheets out upon condensation of vapor and faces the growth medium;
   and a barrier layer positioned over the well, the barrier layer minimizing evaporation from the growth medium.

2. The device of claim 1, wherein the well is shallow enough in order to permit light to pass through the well when the well contains the growth medium for observation with a microscope viewing through the lid.

3. The device of claim 1, wherein the interior side of the lid is coated with a material which prevents fog by causing condensed moisture to sheet out.

4. The device of claim 1, wherein the lid is sealed to the substrate periphery with an adhesive.

5. The device of claim 1, wherein the lid and substrate periphery include an apparatus to provide a mechanical seal between thereof.

6. The device of claim 1, wherein the lid and substrate are sealed by a thermal bond.

7. The device of claim 1, wherein the lid and the substrate are welded by use of a layer of solvent.

8. The device of claim 1, wherein a seal formed between the lid and the substrate prevents an exchange of gas between the well and an environment outside of the seal.

9. The device of claim 1, further including gas passages formed between the top surface and the lid when the two are sealed together communicating with the well and contained within the substrate periphery.

10. The device of claim 9, wherein the gas passages are filled with air.

11. The device of claim 1, wherein the lid is formed of an optically transparent material.

12. The device of claim 11, wherein the lid is formed of a material that is non-toxic to organisms growing in the growth medium.

13. The device of claim 1, wherein the substrate is optically clear in order to transmit light.

14. The device of claim 1, wherein the substrate and well are an integral unit.

15. The device of claim 1, wherein the well periphery is on a lower plane than a substrate periphery plane with respect to the interior side of the lid.

16. The device of claim 1, wherein the substrate is made of an optically clear material.

17. The device of claim 1, wherein the well is formed of a material that is substantially an oxygen and water barrier.

18. The device of claim 1, wherein the barrier layer is made of a material that substantially prevents transmission of oxygen and water.

19. The device of claim 1, wherein the substrate is of sufficient size to be mounted and retained on a microscope for viewing.

20. The device of claim 1, wherein the lid and the substrate are sealed together by a mechnical interlock.

21. A biological culture growth and observation system, comprising:
   a tray with a top and a sealable section on the top, the tray including a depression to receive a growth medium to grow an organism in the depression;
   a lid that is sealable and resealable around the sealable section of the top of the tray defining an interior of the tray, the lid including an interior side facing the growth medium that remains clear for observation, wherein the lid is constructed so as to enable examination and identification of the organism in an interior of the substrate under the lid.

22. The biological culture growth and observation system of claim 21 further comprising, a barrier layer positioned over the depression, the barrier layer minimizing evaporation from the growth medium.

23. The biological culture growth and observation system of claim 21, wherein the depression is shallow enough in order to permit light to pass through the depression when the depression contains the growth medium for observation with a microscope viewing through the lid.

24. The biological culture growth and observation system of claim 21, wherein the interior side of the lid is coated with a material which prevents fog by causing condensed moisture to sheet out.

25. The biological culture growth and observation system of claim 21, wherein the lid is sealed to the sealable section on the top of the tray with an adhesive.

26. The biological culture growth and observation system of claim 21, wherein the lid is mechanically sealed to the sealable section on the top of the tray.

27. The biological culture growth and observation system of claim 21, wherein the lid and the tray are sealed by a thermal bond.

28. The biological culture growth and observation system of claim 21, wherein the lid and the tray are welded by use of a layer of solvent.

29. The biological culture growth and observation system of claim 21, wherein a seal formed between the lid and the tray prevents an exchange of gas between the well and an environment outside of the seal.

30. The biological culture growth and observation system of claim 21, further including gas passages formed between the lid and the top of the tray when the two are sealed together communicating with the depression and contained within the sealable section on the top of the tray.

31. The biological culture growth and observation system of claim 30, wherein the gas passages are filled with air.

32. The biological culture growth and observation system of claim 21, wherein the lid is formed of an optically transparent material.

33. The biological culture growth and observation system of claim 32, wherein the lid is formed of a material that is non-toxic to organisms growing in the growth medium.

34. The biological culture growth and observation system of claim 21, wherein the tray is optically clear in order to transmit light.

35. The biological culture growth and observation system of claim 21, wherein the tray and depression are an integral unit.

36. The biological culture growth and observation system of claim 21, wherein the tray includes a well periphery that is on a lower plane than a tray periphery plane with respect to the interior side of the lid.

37. The biological culture growth and observation system of claim 21, wherein the tray is made of an optically clear material.

38. The biological culture growth and observation system of claim 21, wherein the depression is formed of a material that is substantially an oxygen and water barrier.

39. The biological culture growth and observation system of claim 22, wherein the barrier layer is made of a material that substantially prevents transmission of oxygen and water.

40. The biological culture growth and observation system of claim 21, wherein the tray is of sufficient size to be mounted and retained on a microscope for viewing.

41. The biological culture growth and observation system of claim 21, wherein the lid and the tray are sealed together by a mechnical interlock.

42. A biological culture growth and observation system, comprising:
a tray with a top and a sealable section on the top, the tray including a flat surface to receive a growth medium to grow an organism on the flat surface;
a lid that is sealable and resealable around the sealable section of the top of the tray, the lid including an interior side facing the growth medium that remains clear for observation.

43. The biological culture growth and observation system of claim 42 further comprising, a barrier layer positioned over the flat surface, the barrier layer minimizing evaporation from the growth medium.

44. The biological culture growth and observation system of claim 42, wherein the flat surface is thin enough to permit light to pass through the flat surface when the flat surface contains the growth medium for observation with a microscope viewing through the lid.

45. The biological culture growth and observation system of claim 42, wherein the interior side of the lid is coated with a material which prevents fog by causing condensed moisture to sheet out.

46. The biological culture growth and observation system of claim 42, wherein the lid is sealed to the sealable section on the top of the tray with an adhesive.

47. The biological culture growth and observation system of claim 42, wherein the lid and sealable section of the top include an apparatus to provide a mechanical seal between thereof.

48. The biological culture growth and observation system of claim 42, wherein the lid and the tray are sealed by a thermal bond.

49. The biological culture growth and observation system of claim 42, wherein the lid and the tray are welded by use of a layer of solvent.

50. The biological culture growth and observation system of claim 42, wherein a seal formed between the lid and the tray prevents an exchange of gas between the flat surface and an environment outside of the seal.

51. The biological culture growth and observation system of claim 42, further including gas passages formed between the top of the tray and the lid when the two are sealed together communicating with the flat surface and contained within the sealable section on the top of the tray.

52. The biological culture growth and observation system of claim 42, wherein the gas passages are filled with air.

53. The biological culture growth and observation system of claim 42, wherein the lid is formed of an optically transparent material.

54. The biological culture growth and observation system of claim 53, wherein the lid is formed of a material that is non-toxic to organisms growing in the growth medium.

55. The biological culture growth and observation system of claim 42, wherein the tray is optically clear in order to transmit light.

56. The biological culture growth and observation system of claim 42, wherein the tray is made of an optically clear material.

57. The biological culture growth and observation system of claim 42, wherein the flat surface is formed of a material that is substantially an oxygen and water barrier.

58. The biological culture growth and observation system of claim 43, wherein the barrier layer is made of a material that substantially prevents transmission of oxygen and water.

59. The biological culture growth and observation system of claim 42, wherein the tray is of sufficient size to be mounted and retained on a microscope for viewing.

60. The biological culture growth and observation system of claim 42, wherein the lid and the tray are sealed together by a mechnical interlock.

61. The device of claim 1, further comprising:
a growth medium positioned in the well.

62. The biological culture growth and observation system of claim 21, further comprising:
a growth medium positioned in the depression.

* * * * *